United States Patent [19]

Child et al.

[11] 4,419,354

[45] Dec. 6, 1983

[54] 9,10-BIS(AMINOALKOXY)ANTHRACENES

[75] Inventors: Ralph G. Child, Pearl River; Stanley A. Lang, Jr., Blauvelt, both of N.Y.

[73] Assignee: American Cyanamid Company, Stamford, Conn.

[21] Appl. No.: 384,461

[22] Filed: Jun. 3, 1982

[51] Int. Cl.$^3$ .................. A61K 31/13; A61K 31/535; C07C 93/10; C07D 265/30
[52] U.S. Cl. ............................... 424/248.56; 260/379; 424/250; 424/266; 424/267; 424/274; 424/330; 544/79; 544/357; 546/190; 546/191; 548/523
[58] Field of Search ................ 544/79, 357; 546/190, 546/191; 548/523; 564/352; 424/248.56, 250, 266, 267, 274, 330; 260/379

[56] References Cited

U.S. PATENT DOCUMENTS 4,073,904  2/1978  Fleming et al. ................ 546/191 X

*Primary Examiner*—Richard Raymond
*Attorney, Agent, or Firm*—Edward A. Conroy, Jr.

[57] ABSTRACT

This disclosure describes certain substituted 9,10-bis(2-aminoethoxy)anthracenes which are useful as modulators of the immune response system in warm-blooded animals and for inducing the regression of tumors in such animals.

34 Claims, No Drawings

9,10-BIS(AMINOALKOXY)ANTHRACENES

BRIEF SUMMARY OF THE INVENTION

This invention relates to new organic compounds and, more particularly, is concerned with novel substituted 9,10-bis(2-aminoethoxy)anthracenes which may be represented by the following general formula:

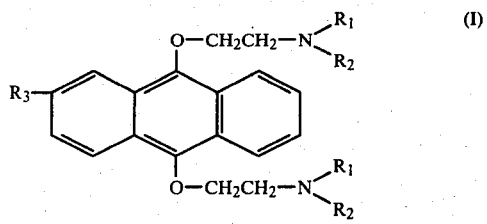

wherein $R_1$ and $R_2$ are each individually selected from the group consisting of hydrogen, alkyl having from one to three carbon atoms and β-hydroxyethyl and $R_1$ and $R_2$ taken together with the associated N(itrogen) is pyrrolidino, morpholino, N-methylpiperazino, piperidino, 2-methylpiperidino, 3-methylpiperidino, 4-methylpiperidino, 3,5-dimethylpiperidino, 4-hydroxypiperidino, 3-hydroxymethylpiperidino or 3-carbethoxypiperidino; and $R_3$ is hydrogen, methyl or chloro.

DETAILED DESCRIPTION OF THE INVENTION

The novel compounds of the present invention are obtainable as crystalline materials having characteristic melting points and absorption spectra and which may be purified by crystalization from common organic solvents. The organic bases of this invention (I) form acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared as set forth in the following reaction scheme:

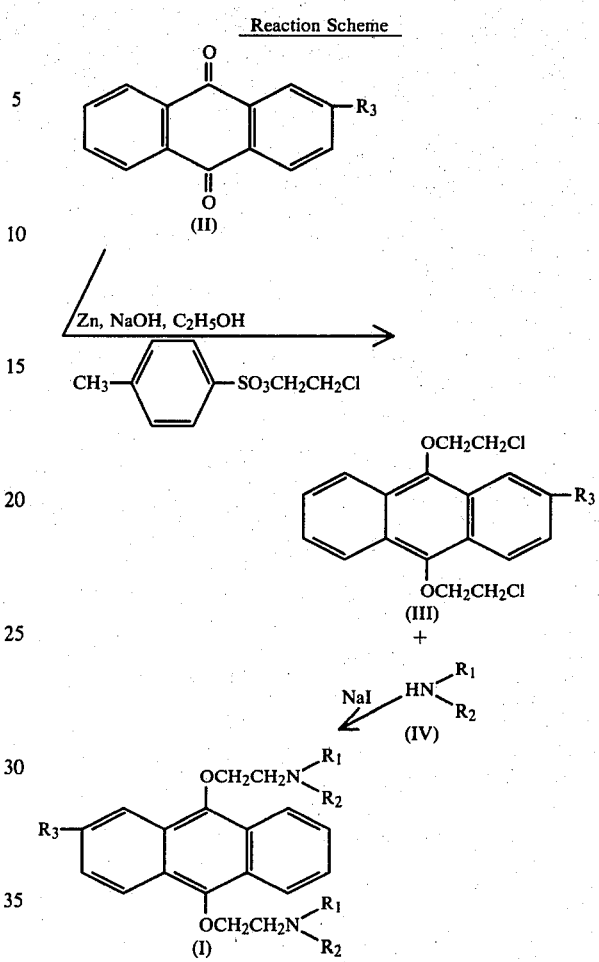

wherein $R_1$, $R_2$ and $R_3$ are as hereinbefore defined.

In accordance with the above reaction scheme, an appropriately substituted anthraquinone, zinc dust, ethanol and dilute sodium hydroxide are combined, heated at reflux for several hours and then treated with 2-chloroethyl-p-toluenesulfonate giving the corresponding 9,10-bis(2-chloroethoxy)anthracene (III). This anthracene is then reacted with the appropriate amine $R_1$, $R_2$ NH (IV) in the presence of sodium iodide and in a suitable solvent at reflux or in a steel bomb at 80°–120° C. for several hours giving the products (I) which may then be converted to acid-addition salts by treatment with anhydrous mineral acid in an alkanol.

The use of immunomodulants and chemotherapeutic adjuvants constitutes a new therapeutic approach to the treatment of immune deficiencies and cancer and is based on the concept that there are distinctive antigents in or on most tumor cells (embryonal or transplantation antigens), that distinguish them from normal host cells. A majority of tumor immunologists favor the view that potentially malignant cells constantly arise but because of their "foreigness" they are normally eliminated by a competent humoral and cellular immune system. Occasionally however, tumor cells escape this immune surveillance and continue to reproduce and cancer results. The reasons for the failure of the normally efficient immune surveillance mechanisms are not fully understood but it is thought that the immune system becomes less effective with increasing age. It is depressed in certain genetic immuno-deficiency diseases, in various bacterial, fungal or viral infections, and in patients undergoing immuno-suppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor remission.

If depression of the immune system can result in the growth of malignancies, regulation of any facet of the immune response may help the host to eliminate residual cancer cells. Therefore, it is desireable to search for chemical agents (i.e., immunoregulants) capable of restoring and stimulating host immune defense mechanisms in order to overcome the deficiencies which account for susceptibility to disease and failure to eradicate the cancer. Such immunoregulating agents would likely be incapable of arresting the growth of a large tumor but their clinical utility would derive from their capacity to enhance normal immune surveillance mechanisms in patients whose tumor burden has been reduced by surgical, radiotherapeutic or chemotherapeutic methods.

Experimental studies in animals have demonstrated the antitumor potential of a number of immunoregulants including live organisms of bacillus Calmett-Guerin (BCG), heat-killed cells of *Corynebacterium parvum,* polynucleotides, and the anthelmintic drug, levamisole. These substances have been shown to stimulate cellular immunity and to produce tumor regression. Some successes have been claimed in early clinical trials with BCG against malignant melanoma and acute leukemia, and with levamisole against lung cancer and breast cancer. Although the anti-tumor effects produced by these agents have been promising, significant therapeutic benefits have yet to be realized. Since this is a new therapeutic approach, new drugs and methods of treatment must receive careful clinical evaluation in order to reveal their full potential.

Modern research is directed to the discovery of a drug similar to, but more potent than, known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infecting mice with a leukemia virus which products both leukemia and a disease-related immunodepression. Effective drugs are recognized by their ability to restore or enhance the antibody response in the experimental mice, or to inhibit tumor progression.

The active compounds and novel compositions of the present invention are active as immunomodulators when tested according to the following procedures:

Inhibition of Splenomegaly and Restoration of Antibody Formation in Mice with Rauscher virus-Induced Leukemia Infection of Balb/c mice with Rauscher leukemia virus (RLV) is characterized by: (1) a rapidly developing viremia, (2) suppression of the primary antibody response to antigens administered a few days after virus infection, (3) a progressive enlargement of the spleen (splenomegaly), and (4) death resulting from splenic rupture and hemmorrhage. The protocol used to infect Balb/c mice with RLV and to test drugs for anticancer and/or immunostimulating activity is as follows:

Day 0: Inject 0.2 ml. intraperitoneally (IP) of a 20% (w/v) RLV-infected spleen cell extract into groups of 5 Balb/c mice. The spleen cell extract is prepared from mice infected with RLV 21 days previously.

Day +6, +7, +8: Test compounds are administered orally in 0.5 ml. of water containing 0.2% Noble agar.

Day +7: Inject 0.5 ml. IP of a thrice saline washed 10% suspension of sheep red blood cells (S-RBC).

Day +14: Bleed mice from the retro-orbital sinus; pool blood from each group. Sacrifice mice, remove and weigh spleens. Serum, harvested from pooled blood of each group of mice is stored at 4° C. for 24 hours. Hemagglutinin tests are performed by standard procedures using a microtiter technique. Acceptable hemagglutinin titer for leukemic (immunosuppressed) mice is $\leq 1:128$. The positive control compound is Poly I:C (polyinosinic acid:polycytidylic acid) administered intraperitoneally on days +6, +7, and +8. Acceptable positive control hemagglutinin titers are 4-fold higher than the titers obtained in leukemic control mice. Average spleen weights of drug treated groups of mice are compared to the average spleen weight of the RLV-infected, placebo treated mice. Reference anticancer agents, cyclophosphamide, 5-fluorouracil, methotrexate, and 6-mercaptopurine consistently produce a 50% or greater reduction in splenomegaly.

Typical compounds of this invention are active in this test, in that they produce a 50% or greater reduction in splenomegaly, and a 4-fold or higher increase in hemagglutinin titer to sheep-RBC's, relative to the placebo treated, RLV-infected control mice. Results of this test appear in Tables I and II.

TABLE I

| Rauscher Virus-Induced Leukemia % Reduction in Splenomegaly | | |
|---|---|---|
| Compound | Dose (mg./kg.) | % Reduction |
| 4,4'-[9,10-Anthrylenebis(oxyethylene)]dimorpholine, dihydrochloride | 200 | 70 |
| 2,2'-(9,10-Anthrylenedioxy)bis-N,N—dimethyl ethylamine, dihydrochloride | 200 | 63 |
| 2,2'-(9,10-Anthrylenedioxy)bis-N,N—diethyl ethylamine, dihydrochloride | 200 | 86 |
| 2,2'-(9,10-Anthrylenedioxy)bis-N—methyl ethylamine, dihydrochloride | 200 | 66 |
| 2,2'-[9,10-Anthrylenebis(oxyethyleneimino)]diethanol, dihydrochloride | 200 | 91 |
| 2,2'-(2-Methyl-9,10-anthrylenedioxy)bis-N,N—diethyl ethylamine, dihydrochloride | 100 | 73 |
| 2,2'-(2-Chloro-9,10-anthrylenedioxy)bis-N,N—diethyl ethylamine, dihydrochloride | 100 | 78 |
| 2,2'-[2-Methyl-9,10-anthrylenebis-(oxyethyleneimino)]di-ethanol, dihydrochloride | 200 | 52 |
| 2,2'-[2-Chloro-9,10-anthrylenebis-(oxyethyleneimino)]di-ethanol, dihydrochloride | 200 | 52 |
| 2,2'-(2-Chloro-9,10-anthrylene)-bis-N—methylethylamine, dihydrochloride | 200 | 55 |
| 1,1'-[9,10-Anthracenediylbis(oxy-2,1-ethanediyl)]bis-3,5-dimethyl-piperidine, dihydrochloride | 400 | 54 |

TABLE I-continued

Rauscher Virus-Induced Leukemia % Reduction in Splenomegaly

| Compound | Dose (mg./kg.) | % Reduction |
|---|---|---|
| 1,1'-[9,10-Anthracenediylbis(oxy-2,1-ethanediyl)]bis-3-piperidine-methanol, dihydrochloride | 100 | 56 |

TABLE II

Antibody Restoration in Mice with Rauscher Virus-Induced Leukemia

| Compound | Dose mg./kg. | Route of Administration | Serum Hemagglutinin Titer/Saline Control Titer |
|---|---|---|---|
| 2,2'-(9,10-Anthrylenedioxy)bis-N,N—dimethyl ethylamine, dihydrochloride | 200 | Oral | 512/64 |
| 2,2'-(9,10-Anthrylenedioxy)bis-N,N—diethyl ethylamine, dihydrochloride | 200 | Oral | 512/64 |
| 2,2'-(9,10-Anthrylenedioxy)bis-N—methyl ethylamine, dihydrochloride | 200 | Oral | 256/64 |
| 2,2'-[9,10-Anthrylenebis(oxyethyleneimino)]-diethanol, dihydrochloride | 200 | Oral | 256/64 |
| 2,2'-(2-Methyl-9,10-anthrylenedioxy)bis-N,N—diethyl ethylamine, dihydrochloride | 50 | Oral | 512/128 |
| 1,1'-[2-Methyl-9,10-anthrylenebis(oxyethylene)]bis-(4-methylpiperazine), tetrahydrochloride | 200 | Oral | 256/64 |
| 1,1'-[9,10-Anthrylenebis-(oxyethylene)]dipiperidine, dihydrochloride | 200 | Oral | 512/64 |
| 3,3'-[9,10-Anthrylenebis(oxyethylene)]dicarbazic acid, diethyl ester | 200 | Oral | 256/64 |
| N,N'—[9,10-Anthrylenebis(oxyethylene)]-bis-propylamine, dihydrochloride | 200 | Oral | 256/64 |
| 1,1'-[2-Methyl-9,10-anthrylenebis(oxyethylene)]dipiperidine, dihydrochloride | 200 | Oral | 256/32 |
| 1,1'-[9,10-Anthracenediylbis(oxy-2,1-ethanediyl)]bis-4-piperidinol, dihydrochloride | 400 | Oral | 256/32 |
| 1,1'-]9,10-Anthracenediylbis(oxy-2,1-ethanediyl)]bis-pyrrolidine, dihydrochloride | 200 | Oral | 256/32 |
| 1,1'-[9,10-Anthracenediylbis(oxy-2,1-ethanediyl)]bis-3-piperidine-methanol, dihydrochloride | 400 | Oral | 256/32 |
| Poly I:C | 10 | ip. | 512/64 |

The active compounds of the present invention possess the property of inhibiting the growth of transplanted mouse tumors as established by the following test.

Lymphocytic leukemia P388 test (intraperitoneal)

The animals used are $BDF_1$ or $CDF_1$ mice, all of one sex, weighing a minimum of 17 grams and all within a 3-gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9; or 1-9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil, dosed at 60 mg./kg. of body weight. The results of this test with typical compounds of the present invention appear in Table III below. The criterion for efficacy is $T/C \times 100 \geqq 125\%$.

TABLE III

Lymphocytic Leukemia P388 Test

| Compound | Dose (mg./kg.) | T/C × 100 (Percent) |
|---|---|---|
| N,N'—[9,10-anthrylenebis(oxyethylene)]bis-propylamine dihydrochloride | 100<br>25 | 128<br>124 |
| 2,2'-(9,10-Anthrylenedioxy)bis-ethylamine dihydrochloride | 25 | 128 |
| 2,2'-[2-Methyl-9,10-anthrylenebis(oxyethyleneimino)]diethanol, dihydrochloride | 50 | 130 |
| 1,1'-[9,10-Anthracenediylbis(oxy-2,1-ethanediyl)]bis-3-methylpiperidine, dihydrochloride | 3 | 127 |
| 1,1'-[9,10-Anthracenediylbis(oxy-2,1-ethanediyl)]bis-3-piperidine-carboxylic acid, diethyl ester, dihydrochloride | 200<br>50<br>12 | 195<br>170<br>130 |

The compounds of the present invention are effective as immunomodulators (that is, they modulate the immune response) when administered orally in amounts ranging from about 5 mg. to about 400 mg. per kilogram of body weight per day. A preferred dosage regimen for optimum results would be from about 5 mg. to about 50 mg. per kilogram of body weight per day, and such dosage units are empolyed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A practical advantage of this convenient manner such as the oral or buccal routes or it may be incorporated directly in the diet.

The compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.5% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

In addition to their utility as modulators of the mammalian immune response system these compounds are also useful as chelating, complexing or sequestering agents. The complexes formed with polyvalent metal ions are particularly stable and usually stable in various organic solvents. These properties render them userful for a variety of purposes wherein metal ion contamination presents a problem, e.g. as stabilizers in various organic systems such as staturated and unsaturated lubricating oils and hydrocarbons, fatty acids and waxes wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds.

The invention will be further described in conjunction with the following examples.

EXAMPLE 1

9,10-Bis(2-chloroethoxy)anthracene

A finely ground mixture of 20.8 g. of anthraquinone, and 10 g. of zinc dust in 40 ml. of ethanol and 200 ml. of 20% sodium hydroxide solution is stirred and heated to reflux for one hour. The solution is then treated portionwise with 2-chloroethyl-p-toluenesulfonate until the dark color is discharged (approx. 50 ml.). After 30 minutes the mixture is cooled, the precipitate is collected and washed with a mixture of 1 N sodium hydroxide and 1 N sodium hydrosulfite until the wash liquid is practically colorless and is then washed with water. The crude yellow solid is crystallized successively from dioxane-water, then propanol, then methylene chloride-methanol, giving 12.4 g. of the desired intermediate as yellow grains, m.p. 143°–145° C.

EXAMPLE 2

4,4'-[9,10-Anthrylenebis(oxyethylene)]dimorpholine, dihydrochloride

A mixture of 1.67 g. of 9,10-bis(2-chloroethoxy)anthracene, one gram of sodium iodide and 50 ml. of morpholine is refluxed for 24 hours. The solution is stripped to dryness on a rotary evaporator, digested with 3 N sodium hydroxide and extracted with three portions of ether. The combined ether extracts are washed twice with water, once with saturated sodium chloride solution, dried over anhydrous magnesium sulfate and treated with 2.5 ml. of 7 N anhydrous hydrochloric acid in isopropanol. The resulting dark oil gradually hardens and is then collected, washed with ether and recrystallized from methanol giving 1.2 g. of the desired product as a colorless solid, m.p. 300°–303° C. (dec.).

EXAMPLE 3

2,2'-(9,10-Anthrylenedioxy)bis(N,N-dimethylethylamine), dihydrochloride

A mixture of 1.67 g. of 9,10-bis(2-chloroethoxy)anthracene, 40 ml. of 40% aqueous dimethylamine, one gram of sodium iodide and 30 ml. of tetrahydrofuran is heated in a steel bomb at 100° C. for 24 hours. After cooling, the clear contents are stripped to dryness, digested with dilute alkali and extracted with ether. The ether extract is washed twice with water, once with saturated sodium chloride solution, dried over anhydrous magnesium sulfate and treated with 2.5 ml. of 7 N anhydrous hydrochloric acid in isopropanol. The resulting oil crystallizes on standing and is recrystallized from methanol, giving 0.85 g. of the desired product as a colorless solid, m.p. 288°–290° C. (dec.).

EXAMPLE 4

2,2'-(9,10-Anthrylenedioxy)bis-N,N-diethyl ethylamine, dihydrochloride

A mixture of 1.67 g. of 9,10-bis(2-chloroethoxy)anthracene, one gram of sodium iodide, 25 ml. of diethylamine, 10 ml. of water and 20 ml. of tetrahydrofuran is heated at 100° C. in a steel bomb for 24 hours. The contents are worked up as described in Example 3. Recrystallization from methanol by the addition of ether gives 2.0 g. of the desired product, m.p. 250°–252° C. (dec.).

EXAMPLE 5

2,2'-(9,10-Anthrylenedioxy)bis(N-methylethylamine, dihydrochloride

A mixture of 1.67 g. of 9,10-bis(2-chloroethoxy)anthracene, 40 ml. of 40% aqueous monomethylamine, one gram of sodium iodide and 30 ml. of tetrahydrofuran is heated in a steel bomb at 80° C. for 24 hours. The contents are worked up as described in Example 3. Recrystallization from methanol gives 0.2 g. of the desired product as a colorless solid, m.p. 300°–304° C. (dec.).

EXAMPLE 6

2,2'[9,10-Anthrylenebis(oxyethyleneimino)]-diethanol, dihydrochloride

A mixture of 1.67 g. of 9,10-bis(2-chloroethoxy)anthracene, 10 ml. of ethanol amine, one gram of sodium iodide, 40 ml. of tetrahydrofuran and 10 ml. of water is heated in a steel bomb at 80°–90° C. for 24 hours. The contents are concentrated to dryness, taken up in water and made basic with 3 N sodium hydroxide, giving a solid which is collected, washed with water and dried. This solid is dissolved in 100 ml. of hot propanol, decolorized with charcoal and treated with 2 ml. of 6 N hydrochloric acid in ethanol giving a solid. This solid is collected, washed with propanol and dried, giving 1.1 g. of the desired product as a cream colored solid, m.p. 250°–255° C.

EXAMPLE 7

9,10-Bis(2-chloroethoxy)-2-methylanthracene

A 22.2 g. portion of 2-methylanthraquinone is reduced with 10 g. of zinc and 200 ml. of 20% sodium hydroxide in 40 ml. of ethanol, then alkylated with 50 ml. of 2-chloroethyl-p-toluene sulfonate as described in Example 1. The crude product is taken up in methylene chloride, filtered, dried over magnesium sulfate and concentrated to dryness. Recrystallization from 100 ml. of propanol gives 0.7 g. of the desired intermediate as a yellow solid, m.p. 82°–85° C.

EXAMPLE 8

2,2'-(2-Methyl-9,10-anthrylenedioxy)bis-N,N-diethyl ethylamine, dihydrochloride

A mixture of 1.75 g. of 9,10-bis(2-chloroethoxy)-2-methyl anthracene, 25 ml. of diethylamine, one gram of sodium iodide, 20 ml. of tetrahydrofuran and 10 ml. of water is heated in a steel bomb at 100° C. for 24 hours. The contents are worked up as described in Example 3. Recrystallization from methanol-ether gives 0.8 g. of the desired product as an off-white solid, m.p. 230°–233° C.

EXAMPLE 9

1,1'-[2-Methyl-9,10-anthrylenebis(oxyethylene)]bis-(4-methylpiperazine), tetrahydrochloride A mixture of 1.75 g. of 9,10-bis(2-chloroethoxy)-2-methylanthracene, 25 ml. of N-methylpiperazine, one gram of sodium iodide and 2 ml. of water is refluxed on an electric mantle for 20 hours and worked up as described in Example 3 giving a crude solid which is recrystallized from methanol, giving 0.6 g. of the desired product, m.p. 275°–278° C. (dec.).

EXAMPLE 10

1,1'-[9,10-Anthrylenebis(oxyethylene)]dipiperidine, dihydrochloride

A mixture of 1.72 g. of 9,10-bis(2-chloroethoxy)anthracene, 50 ml. of piperidine and one gram of sodium iodide is refluxed for 24 hours and worked up as described in Example 3. The crude solid is dissolved in hot methanol, treated with charcoal and filtered. The filtrate is treated with ether giving 2.0 g. of the desired product as a cream colored solid, m.p. 315°–317° C.

EXAMPLE 11

3,3'-[9,10-Anthrylenebis(oxyethylene)]dicarbazic acid, diethyl ester

A mixture of 1.03 g. of 9,10-bis(2-chloroethoxy)anthracene and 30 g. of ethyl carbazate is heated on a hot plate at 130° C. with stirring for 5 hours. The solution is poured into 150 ml. of ice water, stirred and made strongly alkaline with 6 N sodium hydroxide. This mixture is stirred for 15 minutes in ice water, filtered and the solid is washed with water and dried. This solid is recrystallized from 60 ml. of ethanol, giving 1.2 g. of the desired product as a pale yellow solid, m.p. 160°–162° C.

EXAMPLE 12

N,N'-[9,10-Anthrylenebis(oxyethylene)]bis-propylamine, dihydrochloride

A mixture of 1.03 g. of 9,10-bis(2-chloroethoxy)anthracene, 50 ml. of n-propylamine and one gram of sodium iodide is heated in a steel bomb at steam temperature for 20 hours. The contents are worked up as described in Example 3. The crude solid is recrystallized from 200 ml. of methanol, giving 0.2 g. of the desired product as a colorless solid, m.p. 338°–341° C. (dec.).

EXAMPLE 13

2,2'-(9,10-Anthrylenedioxy)bis-ethylamine, dihydrochloride

A mixture of 1.03 g. of 9,10-bis(2-chloroethoxy)anthracene, 50 ml. of ammonia and 20 ml. of tetrahydrofuran is heated in a steel bomb at 125°–140° C. for 20 hours. The contents are worked up as described in Example 3. The crude solid is dissolved in 15 ml. of hot methanol, filtered, treated with 20 ml. of chloroform and cooled, giving 100 mg. of the desired product as a cream colored solid, m.p. 340°–342° C. (dec.).

EXAMPLE 14

2,2'-Benzo[1,2-b:4,5-b']dithiophen-4,8-diyldioxy)bis-N,N-diethyl ethylamine, dihydrochloride An 89.4 g. portion of magnesium turnings is covered with 613 ml. of diethyl ether. A small portion of bromoethane is added to start the reaction, then a mixture of 100 g. of 3-bromothiophene and 334 g. of bromoethane in 1850 ml. of diethyl ether is added dropwise at a rate to maintain gentle reflux. The mixture is refluxed 40 hours, cooled and poured into a mixture of dry ice and ether. The mixture is stirred, then allowed to stand for 2 hours and hydrolysed with 800–1000 ml. of 4 N sulfuric acid. The ether phase is separated and saved. The aqueous phase is extracted with three 500 ml. portions of ether. The ether solutions are combined and extracted with two 500 ml. portions of 2 N sodium hydroxide, then two 400 ml. portions of 1 N sodium hydroxide. The alkaline extracts are combined, cooled and acidified to pH 2.4 with 300 ml. of cool 6 N hydrochloric acid. This mixture is stirred in an ice bath for 1.5 hours and the solid is collected, washed with ice-water and dried, giving 40 g. of 3-thiophene carboxylic acid.

A 100 g. portion of thionyl chloride is added to 34.8 g. of 3-thiophene carboxylic acid. This mixture is stirred and warmed on a steam bath for 15 minutes, then heated at reflux for 45 minutes. The excess thionyl chloride is distilled off and the remaining reaction mixture is fractionated at 32–36 mm. pressure, giving 34.0 g. of 3-thiophene carbonyl chloride.

A 33.5 g. portion of 3-thiophene carbonyl chloride is dissolved in 300 ml. of benzene. A 155 g. portion of dimethylamine is used to prepare a 40% aqueous solution which is cooled to 0° C. and stirred as the above benzene solution is added dropwise over one hour. The mixture is then stirred overnight at room temperature. The benzene layer is separated and saved. The aqueous layer is extracted with four 250 ml. portions of ether. The ether and benzene solutions are combined, washed with 150 ml. of water, dried and concentrated in vacuo to an oily liquid. This liquid is distilled and 30 g. of N,N-dimethyl-3-thiophene carboxamide is collected at 110°–115° C., 1.25 mm. as a liquid.

A 170 g. portion of N,N-dimethyl-3-thiophene carboxamide (prepared as described above) is dissolved in 7 liters of dry ether. A solution of n-butyl lithium in hexane is added dropwise with stirring, maintaining the temperature at less than 28° C. The reaction mixture is cooled and then quenched by pouring into 10 liters of ice and water and stirring for one hour. The solid is collected, washed with 300 ml. of cold water and dried giving 85 g. of crude benzo[1.2-b:4,5-b']dithiophene-4,8-dione. This crude product is purified by column chromatography, giving 69.0 g., m.p. 269°–271° C.

A 5.5 g. portion of benzo[1,2-b:4,5-b']dithiophene-4,8-dione is ground with 2.5 g. of zinc dust, 10 ml. of ethanol and 50 ml. of 5 N sodium hydroxide. This mixture is refluxed for one hour, then treated portionwise with 15 ml. of tosyl chloroethane. The mixture is heated for one hour, cooled and the solid is washed successively with 50 ml. of 1:1 1 N sodium hydroxide:sodium sulfate and then water. The solid is dried, then boiled in 50 ml. of dichloromethane, filtered and stripped to dryness. The residue is crystallized from n-propanol, giving 5.3 g. of 4,8-bis(2-chloroethoxy)benzo[1,2-b:4,5-b]dithiophene.

A mixture of 1.13 g. of 4,8-bis(2-chloroethoxy)benzo[1,2-b:4,5-b]dithiophene, 25 ml. of diethylamine, one gram of sodium iodide, 10 ml. of water and 20 ml. of tetrahydrofuran is heated in a steel bomb at steam bath temperature for 20 hours, stripped to dryness and worked up as described in Example 3, giving 0.95 g. of the desired product as an off-white solid, m.p. 252°–255° C. (dec.).

EXAMPLE 15

2,2'-(Benzo[1,2-b:4,5-b]dithiophen-4,8-diyldioxy)bis(N-methyl-ethylamine), dihydrochloride A mixture of 0.8 g. of 4,8-bis(2-chloroethoxy)benzo[1,2-b:4,5-b']dithiophene, 30 ml. of 40% aqueous methylamine, 0.5 g. of sodium iodide and 20 ml. of tetrahydrofuran is heated in a bomb at steam bath temperature for 20 hours, stripped to dryness and worked up as described in Example 3, giving 0.11 g. of the desired product as a pale yellow solid, m.p. 232°–237° C.

EXAMPLE 16

1,1'[2-Chloro-9,10-anthrylenebis(oxyethylene)]dipiperidine, dihydrochloride

A portion of 2-chloroanthracene is converted to 9,10-bis(2-chloroethoxy)-2-chloroanthracene by the procedure described in Example 1.

A 1.85 g. portion of 2-chloroethoxy-2-chloroanthracene and one gram of sodium iodide in 50 ml. of piperidine is refluxed 24 hours, stripped to dryness and the residue digested with 25 ml. of 3 N sodium hydroxide. The mixture is extracted with three portions of ether which are combined, washed with water, then saturated sodium chloride solution, dried and filtered. The filtrate is treated with 3 ml. of 6 N hydrochloric acid in dry isopropanol giving a solid which is collected, dissolved in 200 ml. of boiling methanol, treated with charcoal, cooled and the solid collected, giving 1.0 g. of the desired product as a cream colored solid, m.p. 298°–303° C.

EXAMPLE 17

2,2'-(2-Chloro-9,10-anthrylenedioxy)bis-N,N-diethyl ethylamine, dihydrochloride

A mixture of 1.85 g. of 2-chloroethoxy-2-chloroanthracene, one gram of sodium iodide, 25 ml. of diethylamine, 20 ml. of tetrahydrofuran and 10 ml. of water is heated in a steel bomb for 24 hours at 100° C. The reaction mixture is stripped of organic solvent and worked up as described in Example 16, giving 2.1 g. of the desired product as pale yellow grains, m.p. 248°–250° C.

EXAMPLE 18

2,2'-[2-Methyl-9,10-anthrylenebis(oxyethyleneimino)]-diethanol, dihydrochloride

A mixture of 1.75 g. of 2-chloroethoxy-2-methylanthracene, 10 ml. of ethanolamine, 40 ml. of tetrahydrofuran, 10 ml. of water and one gram of sodium iodide is heated in a steel bomb at 80°–90° C. for 20 hours and then concentrated to an aqueous solution which is digested with 25 ml. of 3 N sodium hydroxide. The resulting oil is collected, washed with water, dried, taken up in 75 ml. of boiling n-propanol and treated with charcoal. The mixture is filtered and the filtrate treated with 3 ml. of 6 N hydrochloric acid in isopropanol and cooled, giving 1.1 g. of the desired product as a tan solid, m.p. 252°–253° C.

EXAMPLE 19

2,2'-[2-Chloro-9,10-anthrylenebis(oxyethyleneimino)]-diethanol, dihydrochloride

A mixture of 1.85 g. of 2-chloroethoxy-2-chloroanthracene, 10 ml. of ethanolamine, 40 ml. of tetrahydrofuran, 10 ml. of water and one gram of sodium iodide is reacted as described in Example 18. The dihydrochloride salt is recrystallized from a boiling mixture of ethanol and ether, giving 1.4 g. of the desired product as a pale yellow solid, m.p. 258°–260° C.

EXAMPLE 20

1,1'-[2-Methyl-9,10-anthrylenebis(oxyethylene)]-dipiperidine, dihydrochloride

A mixture of 1.75 g. of 2-chloroethoxy-2-methylanthracene, one gram of sodium iodide and 50 ml. of piperidine is reacted as described in Example 16. The dihydrochloride salt is recrystallized by dissolving in 75 ml. of methanol, filtering and treating the filtrate with 75 ml. of ether, giving 2.0 g. of the desired product as a colorless solid, m.p. 314°–316° C. (dec.).

EXAMPLE 21

2,2'-(2-Chloro-9,10-anthrylene)bis-(N-methyl-ethylamine), dihydrochloride

A mixture of 1.85 g. of 2-chloroethoxy-2-chloroanthracene, 40 ml. of 40% aqueous methylamine, 30 ml. of tetrahydrofuran and one gram of sodium iodide is reacted as described in Example 17. The dihydrochloride salt is dissolved in 75 ml. of methanol, filtered and the filtrate is treated warm with 75 ml. of ether, giving 1.5 g. of the desired product as a pale yellow solid, m.p. 296°–298° C.

EXAMPLE 22

1,1'-[9,10-Anthracenediylbis(oxy-2,1-ethanediyl)]bis-3-methylpiperidine, dihydrochloride A mixture of 3.35 g. of 2-chloroethoxyanthracene, 50 ml. of 3-methylpiperidine, and 2.0 g. of sodium iodide is reacted as described in Example 16. The dihydrochloride salt is boiled in 200 ml. of ethanol and the solid is collected by filtration while hot and washed with ethanol, giving 4.0 g. of the desired product, m.p. 298°–300° C.

EXAMPLE 23

N,N'-[9,10-Anthracenediylbis(oxy-2,1-ethanediyl)]bis-3-(1-piperidinyl)-propanamine, tetrahydrochloride A mixture of 3.35 g. of 2-chloroethoxyanthracene, one gram of sodium iodide and 15 g. of piperidinylpropanamine in 125 ml. of n-propanol is refluxed overnight and then stripped to a residual oil. This oil is digested wth 3 N sodium hydroxide solution and extracted with a minimum of ether. The upper of the two ether layers is washed twice with water, then once with saturated sodium chloride solution and then dried and treated with hydrochloric acid in isopropanol. The resulting solid is recrystallized from a mixture of 500 ml. of n-propanol and 200 ml. of methanol, treated with charcoal and cooled, giving 2.0 g. of the desired product as a cream colored solid, m.p. 295°–296° C. (dec.).

EXAMPLE 24

1,1'-[9,10-Anthracenediylbis(oxy-2,1-ethanediyl)]bis-4-methylpiperidine, dihydrochloride A mixture of 3.35 g. of 2-chloroethoxyanthracene, 2.0 g. of sodium iodide and 40 ml. of 4-methylpiperidine is reacted as described in Example 16. The dihydrochloride salt is recrystallized from a mixture of 75 ml. of methanol and 75 ml. of n-propanol with cooling, giving 4.0 g. of the desired product as a colorless solid, m.p. 303°–305° C. (dec.).

EXAMPLE 25

1,1'-[9,10-Anthracenediylbis(oxy-2,1-ethanediyl)]bis-4-piperidinol and its dihydrochloride salt A mixture of 3.35 g. of 2-chloroethoxyanthracene, 2.02 g. of 4-hydroxypiperidine, one gram of sodium iodide and 125 ml. of n-propanol is refluxed for 16 hours and then stripped to dryness. The residue is digested with 3 N sodium hydroxide and stripped to dryness again. This residue is taken up in water, filtered, washed free of sodium hydroxide and dried. The solid is recrystallized from 60 ml. of ethanol with charcoal treatment, giving 3.3 g. of the desired base derivative as pale yellow crystals, m.p. 145°–146° C.

A 3.0 g. portion of the above product is dissolved in 150 ml. of chloroform and treated with an excess of hydrochloric acid in isopropanol giving 3.0 g. of the desired dihydrochloride salt as a colorless solid, m.p. 280°–285° C. (dec.).

EXAMPLE 26

1,1'-[9,10-Anthracenediylbis(oxy-2,1-ethanediyl)]bis-pyrrolidine, dihydrochloride A mixture of 3.35 g. of 2-chloroethoxyanthracene, one gram of sodium iodide and 50 ml. of pyrrolidine is reacted as described in Example 16. The dihydrochloride salt is recrystallized from a mixture of 75 ml. of methanol and 150 ml. of n-propanol, giving 1.0 g. of the desired product as a cream colored solid, m.p. 308°–310° C.

EXAMPLE 27

1,1'-[9,10-Anthracenediylbis(oxy-2,1-ethanediyl)]bis-2-methylpiperidine, dihydrochloride A mixture of 3.35 g. of 2-chloroethoxyanthracene, 2.0 g. of sodium iodide and 40 ml. of 2-methylpiperidine is reacted as described in Example 16. The dihydrochloride salt is dissolved in 30 ml. of methanol and treated with 4–5 times its volume of ether giving 4.4 g. of the desired product as a beige solid, m.p. 260°–263° C. (dec.).

EXAMPLE 28

1,1'-[9,10-Anthracenediylbis(oxy-2,1-ethanediyl)]bis-3,5-dimethylpiperidine and its dihydrochloride salt A mixture of 3.35 g. of 2-chloroethoxyanthracene, 2 g. of sodium iodide and 40 ml. of 3,5-dimethylpiperidine is refluxed for 20 hours, stripped to dryness, digested with 3 N sodium hydroxide and stripped to dryness again. The residue is washed well with water and dried, giving 4.9 g. of the desired base derivative as a beige solid, m.p. 127°–130° C.

A 4.1 g. portion of the above base derivative is dissolved in chloroform, dried over magnesium sulfate and treated with dilute hydrochloric acid in isopropanol. An equal volume of ether is added, giving a solid which is recrystallized from 150 ml. of n-propanol with charcoal treatment, giving 2.7 g. of the desired dihydrochloride salt as yellow crystals, m.p. 286°–287° C. (dec.).

EXAMPLE 29

1,1'-[9,10-Anthracenediylbis(oxy-2,1-ethanediyl)]bis-3-piperidinemethanol, dihydrochloride A mixture of 3.35 g. of 2-chloroethoxyanthracene, 1.0 g. of sodium iodide and 2.3 g. of 3-piperidinemethanol in 125 ml. of n-propanol is refluxed for 20 hours, stripped to dryness, digested with 3 N sodium hydroxide and stripped to dryness again. The oily gum is extracted with chloroform. The chloroform extract is washed with water, then dried over magnesium sulfate and filtered. The filtrate is treated with dilute hydrochloric acid in isopropanol giving an oil. This oil is collected, washed with ether and then triturated in ethanol, giving 4.0 g. of the desired product as an off-white solid, m.p. 265°–267° C. (dec.).

EXAMPLE 30

1,1'-[9,10-Anthracenediylbis(oxy-2,1-ethanediyl)]bis-3-piperidinecarboxylic acid, diethyl ester, dihydrochloride A mixture of 3.35 g. of 2-chloroethoxyanthracene and 30 ml. of ethyl nicotinate is stirred at 125° C. for 7 hours and then cooled. This solution is treated with an equal volume of water, basified with 3 N sodium hydroxide and extracted twice with ether. The combined ether extracts are washed twice with water, once with saturated sodium chloride solution, dried over magnesium sulfate and filtered. The filtrate is treated with dilute hydrochloric acid in isopropanol giving an oil which is washed three times with ether. The oil is taken up in a minimum of n-propanol and then heated with ether giving a solid. This solid is heated in 100 ml. of acetonitrile and filtered while hot, retaining 2.3 g. of the desired product as a colorless solid, m.p. 225°–226° C.

EXAMPLE 31

1,1'-[9,10-Anthracenediylbis(oxy-2,1-ethanediyl)]bispiperidine

A 2.0 g. portion of 1,1'-[9,10-anthrylenebis(oxyethylene)]dipiperidine, dihydrochloride is suspended in 50 ml. of water and basified with saturated sodium bicarbonate solution with stirring. The resulting gum, which hardens on standing, is collected, washed with water and dried. This solid is dissolved in 50 ml. of methanol, filtered and the filtrate treated with an excess of sodium carbonate solution, giving 1.2 g. of the desired product as a cream colored solid, m.p. 103°–106° C.

EXAMPLE 32

Preparation of Compressed Tablet

| Ingredient | mg./Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 33

Preparation of Compressed Tablet—Sustained Action

| Ingredient | mg./Tablet |
|---|---|
| Active Compound as Aluminum Lake, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

EXAMPLE 34

Preparation of Hard Shell Capsule

| Ingredient | mg./Capsule |
|---|---|
| Active Compound | 0.5–500 |
| Lactose, Spray Dried | qs |
| Magnesium Stearate | 1–10 |

EXAMPLE 35

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 36

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 37

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

We claim:

1. A compound selected from the group consisting of those of the formula:

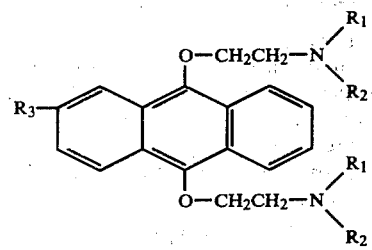

wherein $R_1$ and $R_2$ are the same or different and are hydrogen, alkyl having up to 3 carbon atoms or β-hydroxyethyl and $R_1$ and $R_2$ taken together with the associated N(itrogen) is morpholino, N-methyl piperazino, piperidino, 2-methyl piperidino, 3-methyl piperidino, 4-methyl piperidino, 4-piperidinol, 3,5-dimethyl piperidino, 3-piperidinemethanol, 3-piperidinecarboxylic acid ethyl ester or pyrrolidino; $R_3$ is hydrogen, methyl or chloro; and the pharmacologically acceptable acid-addition salts thereof.

2. The compound according to claim 1, 4,4'-[9,10-anthrylenebis(oxyethylene)]dimorpholine, dihydrochloride.

3. The compound according to claim 1, 2,2'-(9,10-anthrylenedioxy)bis(N,N-dimethylethylamine), dihydrochloride.

4. The compound according to claim 1, 2,2'-(9,10-anthrylenedioxy)bis-N,N-diethyl ethylamine, dihydrochloride.

5. The compound according to claim 1, 2,2'-(9,10-anthrylenedioxy)bis(N-methylethylamine), dihydrochloride.

6. The compound accoding to claim 1, 2,2'-[9,10-anthrylenebis(oxyethyleneimino)]diethanol, dihydrochloride.

7. The compound according to claim 1, 2,2'-(2-methyl-9,10-anthrylenedioxy)bis-N,N-diethyl ethylamine, dihydrochloride.

8. The compound according to claim 1, 1,1'-[2-methyl-9,10-anthrylenebis(oxyethylene)]bis-(4-methylpiperazine), tetrahydrochloride.

9. The compound according to claim 1, 1,1'-[9,10-anthrylenebis(oxyethylene)]dipiperidine, dihydrochloride.

10. The compound 3,3'[],10-anthrylenbis(oxyethylene)]dicarbazic acid, diethyl ester.

11. The compound according to claim 1, N,N'-[9,10-anthrylenebis(oxyethylene)]bis-propylamine, dihydrochloride.

12. The compound according to claim 1, 2,2'-(9,10-anthrylenedioxy)bis-ethylamine, dihydrochloride.

13. The compound according to claim 1, 1,1'-[2-chloro-9,10-anthrylenebis(oxyethylene)] dipiperidine, dihydrochloride.

14. The compound according to claim 1, 2,2'-(2-chloro-9,10-anthrylenedioxy)bis-N,N-diethyl ethylamine, dihydrochloride.

15. The compound according to claim 1, 2,2'-[2-methyl-9,10-anthrylenebis(oxyethyleneimino)]diethanol, dihydrochloride.

16. The compound according to claim 1, 2,2'-[2-chloro-9,10-anthrylenebis(oxyethyleneimino)]diethanol, dihydrochloride.

17. The compound according to claim 1, 1,1'-[2-methyl-9,10-anthrylenebis(oxyethylene)]dipiperidine, dihydrochloride.

18. The compound according to claim 1, 2,2'-(2-chloro-9,10-anthrylene)bis-N-methylethylamine, dihydrochloride.

19. The compound according to claim 1, 1,1'-[9,10-anthracenediylbis(oxy-2,1-ethanediyl)]bis-3-methyl-piperidine, dihydrochloride.

20. The compound N,N'[9,10-anthracendiylbis(oxy-2,1-ethanediyl)]bis-3-(1-piperidiny)-propanamine, tetrahydrochloride.

21. The compound according to claim 1, 1,1'-[9,10-anthracenediylbis(oxy-2,1-ethanediyl)]bis-4-methyl-piperidine, dihydrochloride.

22. The compound according to claim 1, 1,1'-[9,10-anthracenediylbis(oxy-2,1-ethanediyl)]bis-4-piperidinol.

23. The compound according to claim 1, 1,1'-[9,10-anthracenediylbis(oxy-2,1-ethanediyl)]bis-4-piperidinol, dihydrochloride.

24. The compound according to claim 1, 1,1'-[9,10-anthracenediylbis(oxy-2,1-ethanediyl)]bis-pyrrolidine, dihydrochloride.

25. The compound according to claim 1, 1,1'-[9,10-anthracenediylbis(oxy-2,1-ethanediyl)]bis-2-methyl-piperidine, dihydrochloride.

26. The compound according to claim 1, 1,1'-[9,10-anthracenediylbis(oxy-2,1-ethanediyl)]bis-3,5-dimethyl-piperidine.

27. The compound according to claim 1, 1,1'-[9,10-anthracenediylbis(oxy-2,1-ethanediyl)]bis-3,5-dimethyl-piperidine, dihydrochloride.

28. The compound according to claim 1, 1,1'-[9,10-anthracenediylbis(oxy-2,1-ethanediyl)]bis-3-piperidinemethanol, dihydrochloride.

29. The compound according to claim 1, 1,1'-[9,10-anthracenediylbis(oxy-2,1-ethanediyl)]bis-3-piperidinecarboxylic acid, diethyl ester, dihydrochloride.

30. The compound according to claim 1, 1,1'-[9,10-anthracenediylbis(oxy-2,1-ethanediyl)]bis-piperidine.

31. The compound 2,2'-(benzo[1,2-b:4,5-b']dithiophen-4,8-diyldioxy)bis-N,N-diethyl ethylamine, dihydrochloride.

32. The compound 2,2'-(benzo[1,2-b:4,5-b']dithiophen-4,8-diyldioxy)bis-(N-methyl-ethylamine), dihydrochloride.

33. A method of modulating the immune response in a mammal which comprises administering orally to said mammal an effective amount of a compound selected from the group consisting of those of the formula:

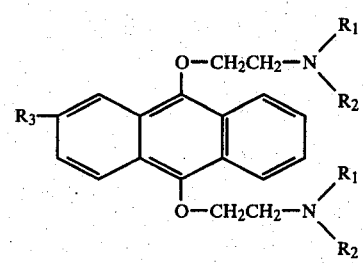

wherein $R_1$ and $R_2$ are the same or different and are hydrogen, alkyl having up to 3 carbon atoms or β-hydroxyethyl and $R_1$ and $R_2$ taken together with the associated N(itrogen) is morpholino, N-methyl piperazino, piperidino, 2-methyl piperidino, 3-methyl piperidino, 4-methyl piperidino, 4-piperidinol, 3,5-dimethyl piperidino, 3-piperidinemethanol, 3-piperidinecarboxylic acid ethyl ester or pyrrolidino; $R_3$ is hydrogen, methyl or chloro; and the pharmacologically acceptable acid-addition salts thereof.

34. A pharmaceutical composition in oral dosage unit form comprising from about 5 to about 400 mg. of a compound of the formula:

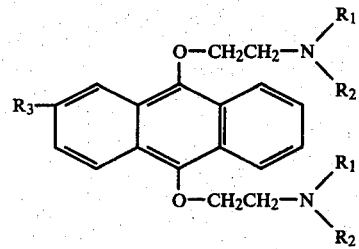

wherein $R_1$ and $R_2$ are the same or different and are hydrogen, alkyl having up to 3 carbon atoms or β-hydroxyethyl and $R_1$ and $R_2$ taken together with the associated N(itrogen) is morpholino, N-methyl piperazino, piperidino, 2-methyl piperidino, 3-methyl piperidino, 4-methyl piperidino, 4-piperidinol, 3,5-dimethyl piperidino, 3-piperidinemethanol, 3-piperidinecarboxylic acid ethyl ester or pyrrolidino; $R_3$ is hydrogen, methyl or chloro; and the pharmacologically acceptable acid-addition salts thereof.

* * * * *